US011305066B2

(12) United States Patent
Dellimore et al.

(10) Patent No.: US 11,305,066 B2
(45) Date of Patent: Apr. 19, 2022

(54) HARVESTING ENERGY FROM OPERATION OF A SYRINGE

(71) Applicant: KONINKLIJKE PHILIPS N.V., Eindhoven (NL)

(72) Inventors: Kiran Hamilton J. Dellimore, Utrecht (NL); Arthur Bouwman, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 224 days.

(21) Appl. No.: 16/621,726

(22) PCT Filed: Jun. 6, 2018

(86) PCT No.: PCT/EP2018/064821
§ 371 (c)(1),
(2) Date: Dec. 12, 2019

(87) PCT Pub. No.: WO2018/228876
PCT Pub. Date: Dec. 20, 2018

(65) Prior Publication Data
US 2020/0129701 A1 Apr. 30, 2020

(30) Foreign Application Priority Data

Jun. 15, 2017 (EP) .................................... 17176225

(51) Int. Cl.
*A61M 5/31* (2006.01)
*H02K 7/18* (2006.01)

(52) U.S. Cl.
CPC ............ *A61M 5/31* (2013.01); *H02K 7/1869* (2013.01); *A61M 2005/3125* (2013.01);
(Continued)

(58) Field of Classification Search
CPC ............ A61M 5/31; A61M 2005/3125; A61M 2205/3317; A61M 2205/3389;
(Continued)

(56) References Cited

U.S. PATENT DOCUMENTS

| 4,737,151 A | 4/1988 | Clement |
| 5,176,642 A | 1/1993 | Clement |

(Continued)

FOREIGN PATENT DOCUMENTS

| EP | 2283881 A2 | 2/2011 |
| WO | 2016162298 A1 | 10/2016 |

OTHER PUBLICATIONS

Jansen, A., "Human Power empirically explored", 2011, The Netherlands.

(Continued)

*Primary Examiner* — Lauren P Farrar (57) ABSTRACT

Various methods and apparatus disclosed herein relate to apparatus and techniques for harvesting energy from operation of a syringe, and utilizing that energy for various purposes. In various embodiments, a method (400) for harvesting and using electrical energy during operation of a syringe (100, 300) may include: operating (402) the syringe, wherein operating includes displacing a plunger (112) of the syringe to draw fluid into a reservoir (114) of the syringe or expel fluid from the reservoir of the syringe; converting (404), by an electrical generator (120, 122) that is integral with the syringe, motion associated with displacing the plunger into electrical energy; and using (406) at least some of the electrical energy to at least temporarily store, in a memory component (136) integral with the syringe, one or more data points associated with operation of the syringe.

13 Claims, 4 Drawing Sheets

(52) U.S. Cl.
CPC ............... *A61M 2205/3317* (2013.01); *A61M 2205/3389* (2013.01); *A61M 2205/3584* (2013.01); *A61M 2205/52* (2013.01); *A61M 2205/825* (2013.01)

(58) Field of Classification Search
CPC ...... A61M 2205/3584; A61M 2205/52; A61M 2205/825; A61M 2205/82; A61M 5/1456; A61M 5/20; A61M 5/1424; A61M 5/1452; H02K 7/1869
See application file for complete search history.

(56) References Cited

U.S. PATENT DOCUMENTS

| | | | |
|---|---|---|---|
| 8,382,703 | B1 | 2/2013 | Abdelaal |
| 2006/0063522 | A1* | 3/2006 | McFarland ............... H04Q 9/00 455/423 |
| 2009/0216292 | A1* | 8/2009 | Pless .................... A61N 1/3785 607/33 |
| 2011/0009812 | A1 | 1/2011 | Brown |
| 2011/0111794 | A1 | 5/2011 | Bochenko et al. |
| 2011/0264033 | A1 | 10/2011 | Jensen et al. |
| 2013/0317626 | A1 | 11/2013 | Loverich et al. |
| 2015/0045727 | A1 | 2/2015 | Bammer et al. |
| 2018/0135801 | A1 | 5/2018 | Franklin |

OTHER PUBLICATIONS

Guldahl, A., "Minimizing energy consumption in capacitive sensing applications", Energy Micro, 2012.
"Breakout of the US market for syringes", Google answers, Accessed Dec. 5, 2019.
"A Clinical Reminder About the Safe Use of Insulin Vials", Institute for Safe Medication Practices, Feb. 21, 2013.
Neely, A., "Persistence of microorganisms on common hospital surfaces: Strategies to control their dissemination", Infection Control Resource, vol. 4, No. 4, Accessed Dec. 5, 2019.
Mannion, P., "Comparing Low-Power Wireless Technologies (Part 1)", Digi-Key Electronics, Oct. 26, 2017.
Eink, https://www.eink.com/benefits-of-eink-technology.html, Accessed Dec. 5, 2019.
E ink display, https://wiki.mobileread.com/wiki/E_Ink_display, Accessed Dec. 5, 2019.
International Search Report and Written Opinion, International Application No. PCT/EP2018/064821, dated Jul. 4, 2018.

* cited by examiner

HARVESTING ENERGY FROM OPERATION OF A SYRINGE

CROSS-REFERENCE TO PRIOR APPLICATIONS

This application is the U.S. National Phase application under 35 U.S.C. § 371 of International Application No. PCT/EP2018/064821, filed on 6 Jun. 2018, which claims the benefit of European Patent Application No. 17176225.5, filed on 15 Jun. 2017. These applications are hereby incorporated by reference herein.

TECHNICAL FIELD

The present invention is directed generally to health care. More particularly, various methods and apparatus disclosed herein relate to apparatus and techniques for harvesting energy from operation of a syringe, and utilizing that energy for various purposes.

BACKGROUND

Manually-driven syringes are used ubiquitously in a variety of clinical settings such as emergency rooms, intensive care units ("ICU"), general wards, and elsewhere. Syringes may be used for a broad range of applications such as medication administration and bodily fluid collection. Syringes may also be used outside of clinical settings, such as in the home, e.g., by individuals with diabetes mellitus who must take regular insulin shots. Syringes enable fluids to be injected into and/or withdrawn from patients intravenously, intramuscularly, and/or subcutaneously.

Conventional manually-driven syringes suffer from a variety of shortcomings. Syringes may be inadequately and/or inaccurately labeled, before and/or after use. This can make tracking administration of medication using syringes onerous for busy medical personnel. It is not uncommon for syringes to be used incorrectly, and a general inability to precisely track medication administration/use may lead to incorrect dosage. Additionally, without ensuring that syringes are only used once, or that they are at least sanitized between uses, there is risk of cross contamination.

U.S. Pat. No. 8,382,703 B1 discloses piezo an electric dual-syringe insulin pump including a single piezoelectric motor configured to pump insulin. The pump is controlled by a single controller. The pump uses two insulin reservoirs (in the form of two syringes), one of which is filled with a rapid-acting insulin, the other reservoir being filled with slow-acting insulin.

U.S. Pat. No. 4,737,151 A discloses a syringe injector for holding a syringe that comprises a barrel and a plunger. The plunger includes a piston received in the barrel. The injector comprises a support frame with a cradle to receive the syringe barrel at one end of the support frame.

EP 2283881 A2 discloses a wearable, self-contained drug infusion or medical device capable of communicating with a host controller or other external devices via a personal area network (PAN). The medical device utilizes a PAN transceiver for communication with other devices in contact with a user's body, such as a physiological sensor or host controller, by propagating a current across the user's body via capacitive coupling.

WO 2016/162298 A1 discloses a portable module for detecting an infusion of the contents of a syringe when the portable module is attached to said syringe, the syringe comprising a barrel extending in a longitudinal direction and a plunger seal adapted to slide inside the barrel along said direction.

SUMMARY

The present disclosure is directed to methods and apparatus for harvesting energy from operation of a syringe, and utilizing that energy for various purposes. For example, in various embodiments, motion associated with displacement of a syringe plunger (to inject and/or draw fluids) may be converted, e.g., using an alternator or other similar means, to electrical energy. The electrical energy may be stored in a capacitor or other similar energy storage means. In various embodiments, the stored electrical energy may be used to acquire data such as a fill level of the syringe (e.g., dosage) and store that data in memory, wirelessly transmit that data to a remote computing device, render information on a low power display (e.g., E-ink), cause one or more alerts to be raised using output devices of the syringe itself or of remote computing devices, and so forth.

Generally, in one aspect, a method for harvesting and using electrical energy during operation of a syringe may include: operating the syringe, wherein operating may include displacing a plunger of the syringe to draw fluid into a reservoir of the syringe or expel fluid from the reservoir of the syringe; converting, by an electrical generator that is integral with the syringe, motion associated with displacing the plunger into electrical energy; and using at least some of the electrical energy to at least temporarily store, in a memory component integral with the syringe, one or more data points associated with operation of the syringe.

In various embodiments, the operating may include displacing the plunger of the syringe to draw fluid into the reservoir, and the method further comprises measuring a fill level of the reservoir. In various embodiments, the one or more data points may include the fill level. In various embodiments, measuring the fill level of the reservoir may include detecting a capacitance of a capacitor contained within the reservoir.

In various embodiments, the operating may include displacing the plunger of the syringe to expel fluid from the reservoir. In various embodiments, the method ma further include utilizing at least some of the electrical energy to wirelessly transmit, from a low power wireless transceiver integral with the syringe to a remote computing device, one or more of the data points. In various embodiments, the low power wireless transceiver may be a Bluetooth low energy transceiver or a ZigBee transceiver.

In various embodiments, the method may further include utilizing at least some of the electrical energy to render, on a low power display integral with the syringe, one or more of the data points. In various embodiments, the method may further include utilizing at least some of the electrical energy to wirelessly receive, at a low power wireless transceiver integral with the syringe from a remote computing device, a timestamp.

In another aspect, in various embodiments, an energy harvesting syringe may include: a housing; a plunger that is displaceable relative to the housing to draw fluid into a reservoir or to expel fluid from the reservoir; an electrical generator integral with the syringe, wherein the electrical generator converts motion associated with displacement of the plunger into electrical energy; and a memory component integral with the syringe, wherein the memory component is powered by at least some of the electrical energy to store one or more data points associated with operation of the syringe.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Conventional manually-driven syringes suffer from a variety of shortcomings. Syringes may be inadequately and/or inaccurately labeled, before and/or after use. This can make tracking administration of medication using syringes onerous for busy medical personnel. It is not uncommon for syringes to be used incorrectly, and a general inability to precisely track medication administration/use may lead to incorrect dosage. Additionally, without ensuring that syringes are only used once, or that they are at least sanitized between uses, there is risk of cross contamination. In view of the foregoing, various embodiments and implementations of the present invention are directed to for harvesting energy from operation of a syringe, and utilizing that energy for various purposes.

Figure 1:
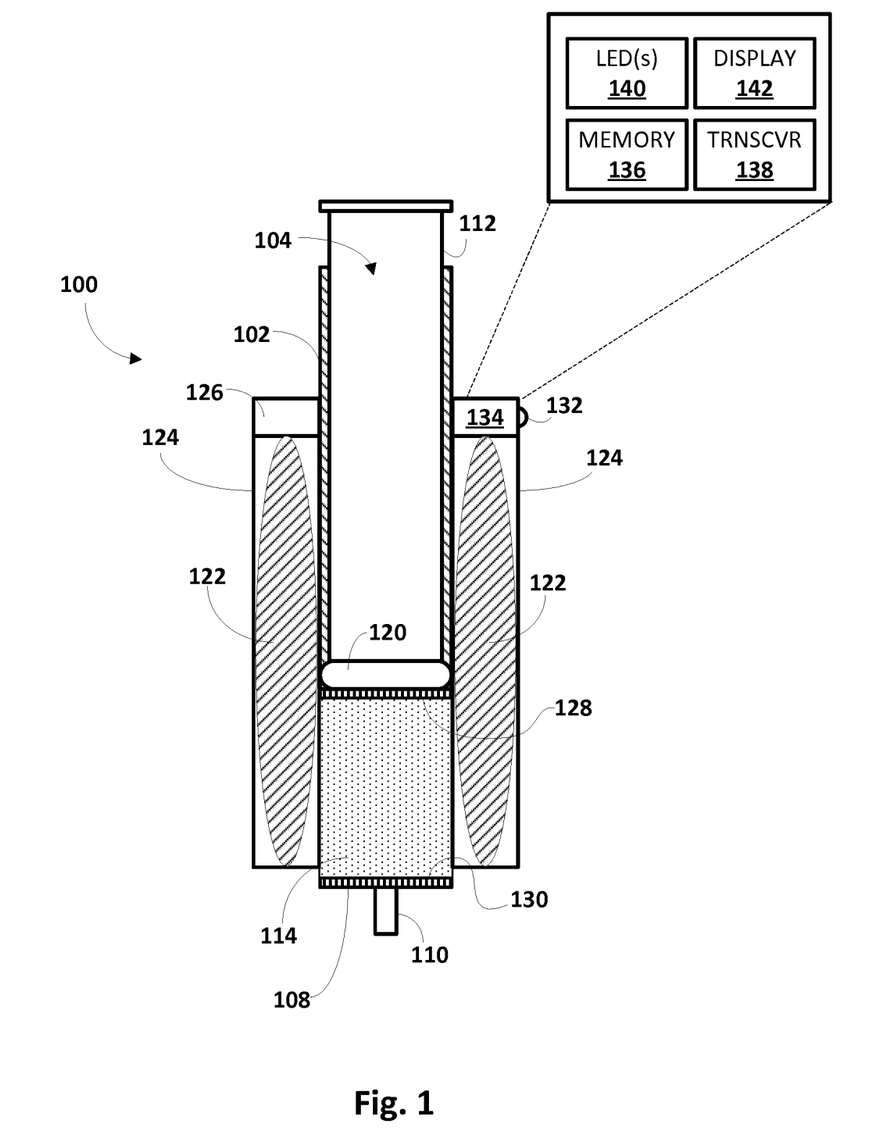
FIG. 1 illustrates an example manually-driven syringe configured with selected aspects of the disclosure, in accordance with various embodiments.

Referring to FIG. 1, an example energy-harvesting syringe 100 configured with selected aspects of the present disclosure is depicted in cross section. Syringe 100 may include an outer housing 102 (sometimes referred to as a "barrel") that includes an interior 104. Housing 102 may include, at a distal end 108, a tip 110. While depicted as a simple exit port in FIG. 1 (e.g., for administration of medicine orally), tip 110 may take various forms, such as a hypodermic needle, a jet injection port (e.g., for needleless subcutaneous injection), and so forth.

A plunger 112 (sometimes referred to as a "piston") may be situated at least partially within interior 104 and may be displaceable along a longitudinal axis of housing 102 (up and down in FIG. 1) to define a reservoir 114 having a volume that is determined based on a position of plunger 112 relative to housing 102. As plunger 112 is withdrawn from housing 102 (i.e., displaced upwards in FIG. 1), reservoir 114 may grow in volume and may draw in fluid assuming tip 110 is inserted to a container of liquid medicine or in tissue. Likewise, as plunger 112 is driven into housing 102 (i.e., displaced downward in FIG. 1), reservoir 114 may decrease in volume and fluid contained therein may be expelled through tip 110.

As noted above, embodiments described herein are generally directed to harvesting energy during operation of syringes and utilizing the harvested energy for various purposes. Accordingly, syringe 100 may include a variety of integral components that facilitate conversion of motion associated with displacement of plunger 112, e.g., to draw fluid into reservoir 114 and/or to expel fluid from reservoir 114, into electrical energy. In the example depicted in FIG. 1, for instance, a ferromagnetic element 120 is disposed on plunger 112, e.g., at or near a distal tip. A series of conductive coils 122 are also wrapped around a portion of housing 102, e.g., in a sleeve 124 that wraps around housing 102. Displacement of plunger 112 may cause corresponding displacement of ferromagnetic element 120 relative to conductive coils 122. According to Faraday's Law, the movement of ferromagnetic element 120 relative to conductive coils 122 may induce a current in conductive coils 122. The flow of electrons forming this current may, for instance, charge a capacitor 126 with electrical energy, which may then used for a variety of purposes. In some embodiments, the components described above may be retrofitted to conventional syringes. For example, as depicted in FIG. 1, many of the components (e.g., onboard circuitry 134, capacitor 126, conductive coils 122) may be disposed on or within sleeve 124, which may be formed as an external housing. Such a sleeve 124 may be placed around a housing of a conventional syringe in order to retrofit the conventional syringe to be configured with selected aspects of the present disclosure.

One non-limiting purpose for which the harvested electrical energy may be used is measuring a fill level of reservoir 114. In some embodiments, a first capacitive electrode 128 may be disposed on or near a tip of plunger 112, and a second capacitive electrode 130 may be disposed within interior 104 of housing 102 near distal end 108. When plunger 112 is withdrawn from housing 102 to draw fluid into reservoir 114, electrical energy is harvested within capacitor 126 as described above. Once the user has drawn sufficient fluid into reservoir 114 and thereby has stopped withdrawing plunger 112 from housing 102, the harvested electrical energy may be discharged, e.g., in response to a user operating an actuator 132 (e.g., a button or switch), to determine a capacitance between the first and second capacitive electrodes 128, 130. This measured capacitance may be indicative of a fill level of reservoir 114.

In various embodiments, syringe 100 may include onboard circuitry 134 that may include, for instance, some form of rudimentary memory component 136 for storing one or more data points associated with operation of syringe 100. For example, in some embodiments, the capacitive fill level determined above may be stored at least temporarily in memory component 136. Memory component 136 may take various forms that may or may not be considered "low power" because only a minimal amount of electrical energy is required to read from, and/or write to the memory component. In some embodiments, memory component 136 may be non-volatile, and may include one or more of the following: random access memory ("RAM"), programmable ready-only memory ("PROM"), erasable PROM ("EPROM"), electrically erasable PROM ("EEPROM"), flash memory (NAND or NOR), Ferroelectric RAM ("FeRAM"), Programmable metallization cell ("CBRAM"), parallel random-access machine ("PRAM"), Silicon-Oxide-Nitride-Oxide-Silicon ("SONOS"), Resistive random-access memory ("RRAM"), racetrack memory, Nano-RAM, and so forth.

In some embodiments, onboard circuitry 134 may also include a transceiver 138 (or in some cases, simply a transmitter), e.g., operably coupled with memory component 136. Transceiver 138 may be configured to communicate wirelessly with remote computing devices (not depicted in FIG. 1) using various low energy wireless technologies, such as Bluetooth low energy (e.g., Bluetooth 4.0), ANT, ANT+, infrared data association ("IrDA"), ZigBee, Z-Wave, low power Wi-Fi, near field communication ("NFC"), EnOcean radiofrequency transmission protocol, and so forth. In various embodiments, one or more data points stored at least temporarily in memory component 136 may be transmitted by transceiver 138 to one or more remote computing devices, such as a mobile device (e.g., smart phone, laptop, tablet, wearable device) operated by a user (e.g., a patient and/or medical personnel). For example, the capacitive fill level described previously may be transmitted to a mobile device carried by medical personnel administering medication (or withdrawing fluids) using syringe 100. In some embodiments, electrical energy harvested during displacement of plunger 112 into interior 104 to expel fluids from reservoir 114 may be used to power wireless transmission of such data to one or more remote computing devices. In some embodiments, the mobile device may store the data point(s), e.g., in association with a timestamp generated by and received from the mobile device.

Assume that when plunger 112 is displaced to expel fluid from reservoir 114 (or to draw fluid into reservoir 114), a force F of 15-25 N is applied. Application of such a force F over a bi-directional distance D of 50-100 mm during operation of syringe 100 may yield the following equation to calculate (gross) harvested energy $E_{gross}$:

$$E_{gross}=F \times D=(15\text{-}25 \text{ N})*(0.050\text{-}0.100 \text{ m})=0.750\text{-}2.500 \text{ J} \qquad (1)$$

Even accounting for 40% energy loss, the net energy harvested $E_{net}$ may be estimated as follows:

$$E_{net}=0.6*E_{gross}=0.6*(0.750\text{-}2.500)=0.450\text{-}1.50 \text{ J} \qquad (2)$$

A simple energy budget calculation may be used to confirm that the net energy generated $E_{net}$ is sufficient to transmit one or more data points using transceiver 138 is harvested:

$$E_{net} \geq E_{gross}-(E_{DA}+E_{DS}+E_{xmit}+E_{loss}) \qquad (3)$$

$E_{DA}$ represents energy required to perform data acquisition (e.g., capacitive fill measurement). $E_{DS}$ represents energy required to at least temporarily store one or more data points. $E_{xmit}$ represents energy required to transmit the one or more data points. $E_{loss}$ represents energy losses, which assuming 40% energy losses, may be calculated as $0.4 \times E_{gross}$.

Suppose that ZigBee or low-power Wi-Fi is employed for wireless transmission, and that estimated energy losses are 40%. The sum of energy consumed during data acquisition $E_{DA}$ (which may be assumed to be 1.2-150 μA for capacitive fill measurement) and energy consumed during temporary storage $E_{DS}$ may be approximately 0.250 J. In some embodiments, 0.036 J of electrical energy $E_{xmit}$ may be consumed during data transmission (power requirement for low-power Wi-Fi/ZigBee is 36 mJ per 24 bytes of data. For Bluetooth low energy it is less, 0.147 mJ). Suppose $E_{gross}$ is 0.75 J, which means $E_{loss}$ is 0.3 J. Plugging the values set forth above into Equation (3) shows that there is sufficient net energy $E_{net}$ to acquire, store, and transmit data:

$$0.45 \geq 0.750 \text{ J}-(0.250 \text{ J}+0.036 \text{ J} \pm 0.300 \text{ J})=0.164 \text{ J} \qquad (4)$$

The equations above are examples only, and are not meant to be limiting. Even more energy may be generated if syringe 100 is longer, or if greater forces are used to displace plunger 112, which can be accomplished by varying the frictional resistance of an interior surface of housing 102.

In some embodiments, syringe 100 may include (e.g., coupled with onboard circuitry 134 and depicted schematically in FIG. 1) one or more output devices, such as one or more light-emitting diodes ("LEDs") 140 and/or a display 142. While only depicted schematically in FIG. 1, these output components may be located at various positions on syringe 100, such as on a portion of housing 102, on a proximal end of plunger 112 (i.e. the top in FIG. 1), and so forth. In some such embodiments, one or more LEDs 140 may be illuminated (e.g., with a red color), for instance, after syringe 100 is used. At least some of the electrical energy harvested during operation of syringe may be used to energize one or more LEDs 140 to indicate that, for instance, syringe 100 has been used and should not be reused (or should not be used again without being sanitized first). Such a simple indicator may be particularly useful when, for instance, medical personnel are in a chaotic situation such as a disaster, busy ward, etc., in which they are likely to become distracted.

Display 142 may take various forms of low power displays, such as an E-ink display, or a small coarse LED light display (e.g., covering an area that may be smaller than, for instance, 20 mm by 20 mm). E-ink screens may only require a small amount of electrical energy, such as 20-25 mW to power a 20 mm by 20 mm screen to render information. In addition, E-ink screens may not require additional electrical energy once an image has been rendered. Thus, for example, once a fill volume (detected, for instance, using capacitive fill measurement sampling described above) and a time (e.g., timestamp received via transceiver 138 from a remote computing device) are rendered, those data points may remain on the E-ink screen without requiring additional electrical energy.

Figure 2:
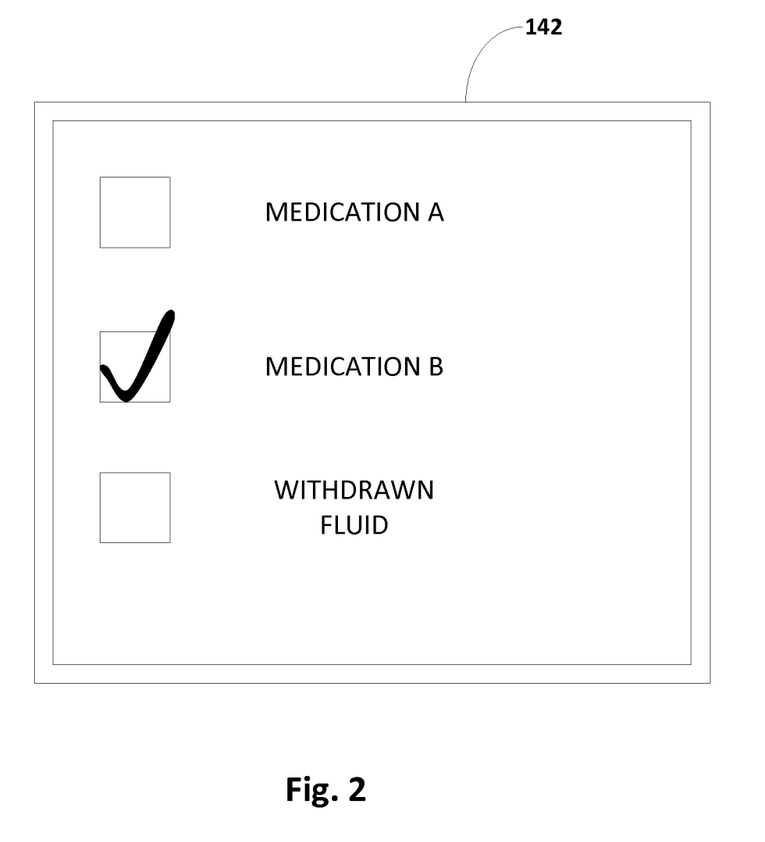
FIG. 2 depicts an example low power display that may be integrated with a syringe configured with selected aspects of the present disclosure, in accordance with various embodiments.

In some embodiments, an E-ink display 142 or other similar display may be configured to be writable by a user. For example, and referring to FIG. 2, a display 142 is depicted that includes three predefined user input fields or indicia for MEDICINE A, MEDICINE B, and WITHDRAWN FLUID. Such information may be displayed, for instance, in a scenario in which only those two medications are being administered, or fluid is being withdrawn. In some embodiments, the text on the display may be passive indicia that is printed, painted, and/or adhered to display, e.g., as stickers. Portions of display 142 (e.g., within the check boxes) may be writeable, as indicated by the check in the middle box. In other embodiments, the text on the display may be rendered, e.g., using E-ink. Medical personnel may check the box or boxes for which syringe 100 has been used, or for which syringe 100 is intended to be used. This may avoid accidental cross contamination and other mishaps that might be more likely without the ability to label syringe 100. In some embodiments, display 142 may be used to render a Quick Response (QR) code, bar code, or other information that indicates how syringe 100 has or will be used.

Figure 3:
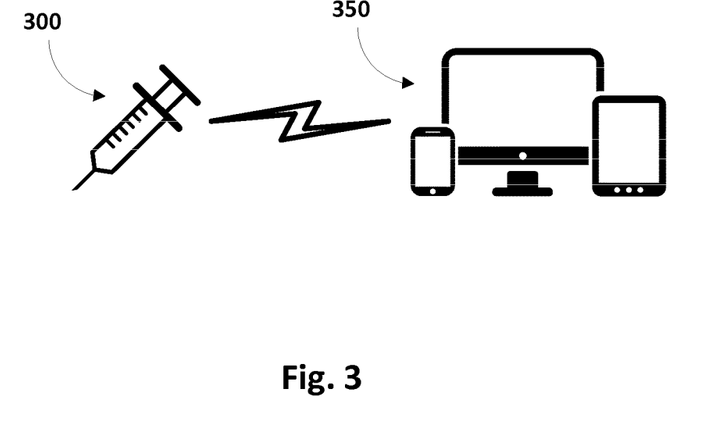
FIG. 3 schematically depicts an environment in which a syringe configured with selected aspects of the present disclosure may wirelessly exchange data with one or more computing devices, e.g., operated by medical personnel or other users.

FIG. 3 schematically depicts an environment in which a syringe 300 configured with selected aspects of the present disclosure may wirelessly exchange data with one or more computing devices 350 (e.g., smart phones, tablets, laptops, wearable devices, etc.), e.g., operated by medical personnel or other users. In some such embodiments, syringe 300 may store (e.g., in memory using energy harvested during operation) an indication that syringe 300 has been used, e.g., to administer medication or withdraw fluids. That indication may be wirelessly transmitted from syringe 300 to one or more remote computing devices 350. Should medical personnel attempt to reuse syringe 300, circuitry on syringe 300 may raise a wireless alert to one or more remote computing devices 350, which may provide audible, visual, and/or haptic feedback indicating that syringe 300 should not be reused.

In other embodiments, one or more remote computing devices 350 may wirelessly receive, from syringe 300, information about dosage to be administered or already administered (e.g., determined based on the capacitive fill measurement described above). The remote computing device 350 may determine a time at which the dosage was administered or will be administered, e.g., via a timestamp generated contemporaneously with receiving the data wirelessly from syringe 300. Remote computing device 350 may then compare the dosage and/or time to a prescribed dosage and/or time, e.g., by consulting one or more electronic medical records ("EMRs"). If the actual/intended dosage/time does not comport with the prescribed dosage/time, remote computing device 350 may raise an alert, e.g., by providing audio, visual, and/or haptic feedback, by sending medical personnel or others a text message, and so forth. In some embodiments, if remote computing device 350 has not received, from syringe 300, an indication that a dose of medication has been administered when prescribed (or a sample of fluid withdrawn at a predetermined time), remote computing device 350 similarly may raise an alert, which may include audio, visual, and/or haptic feedback to remind a user to administer the medication (or withdraw the fluid).

In general, automatically harvesting energy as described herein and using that energy to store information about dosage, time administered, volume of fluid withdrawn, etc., and/or to make that information available on one or more remote computing devices, may have a number of technical advantages. Medical personnel may be relieved of at least some of the burden of documenting when dosage was administered and/or when fluid was withdrawn. This may in turn reduce errors that might otherwise result from distractions, etc. This also may allocate time medical personnel would have otherwise spent performing data entry to perform other tasks, e.g., treating other patients. Techniques described herein also decrease the likelihood of a patient receiving an incorrect medication, or of a fluid being incorrectly or mistakenly withdrawn. Techniques described herein may also aid outpatients such as diabetes patients that must take insulin periodically with ensuring that they follow a prescribed treatment regimen.

Figure 4:
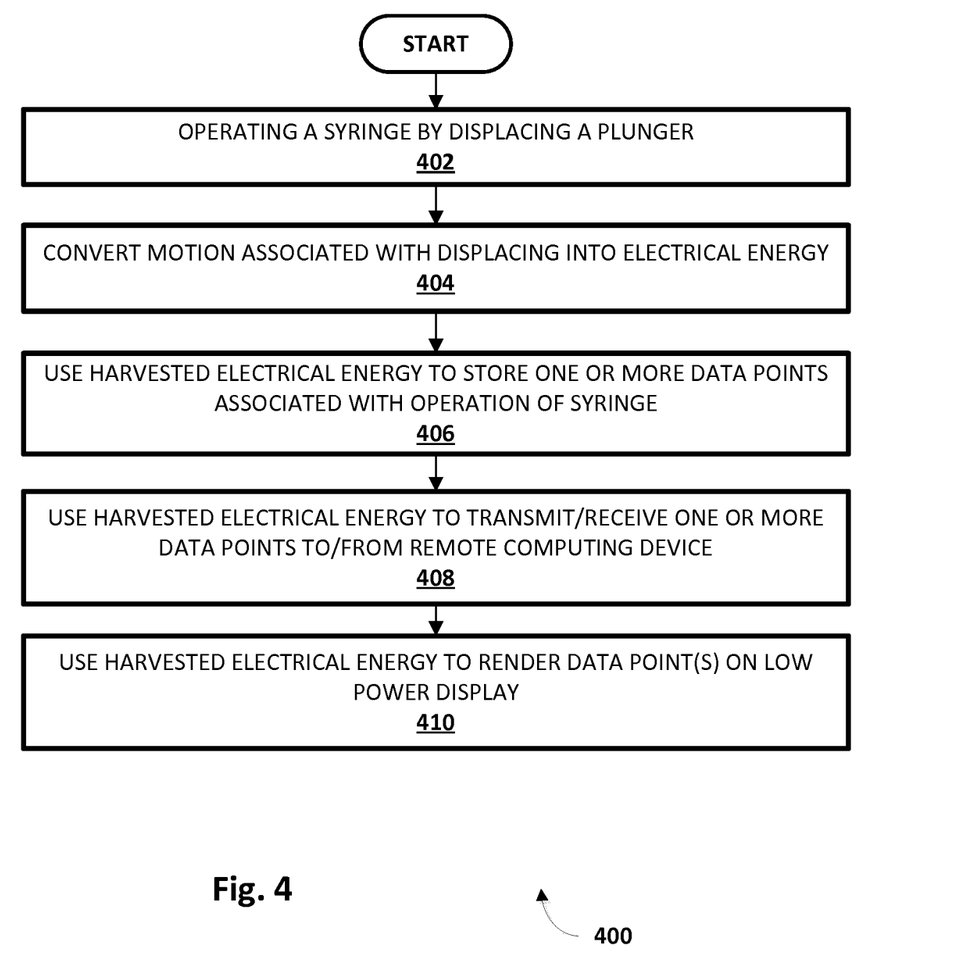
FIG. 4 depicts an example method of performing various techniques described herein, in accordance with various embodiments.

FIG. 4 depicts an example method 400 of performing various techniques described herein, in accordance with various embodiments. Although particular operations of method 400 are shown in a particular order, this is not meant to be limiting. In various embodiments, one or more operations may be added, omitted, and/or reordered.

At block 402, a syringe configured with selected aspects of the present disclosure may be operated by displacing the plunger (e.g., 112) relative to a housing (e.g., 102). In some embodiments, the plunger may be displaced to expel fluid from a reservoir (e.g., 114), e.g., to administer medication and/or to prime the syringe to draw fluid. In other embodiments, the plunger may be displaced to draw fluids such as blood, interstitial fluid, etc. from a patient's tissue. At block 404, motion associated with the displacement may be converted, e.g., by an alternator and/or other components (e.g., the components depicted in FIG. 1), into electrical energy. In this manner, electrical energy may be harvested during operation of the syringe.

At block 406, at least some of the electrical energy harvested during operation of the syringe may be used to at least temporarily store one or more data points in a memory component 136 that is integral with the syringe. These data points may include, but are not limited to, capacitive fill measurements, fill measurements obtained using other means (e.g., user input, magnetically detected, float-detected, gravity-detected, etc.), timestamps (e.g., received from a remote computing device), type of medication administered (which may or may not be user input), type of fluid withdrawn (which may or may not be user input), and so forth.

At block 408, at least some of the electrical energy harvested during operation of the syringe may be used to transmit one or more of the aforementioned data points to a remote computing device. Additionally or alternatively, in some embodiments, at least some of the electrical energy harvested during operation of the syringe may be used to power a receiver (e.g., transceiver 138) to receive one or more data points (e.g., a time stamp, medication identifier, etc.) from a remote computing device. At block 410, at least some of the electrical energy harvested during operation of the syringe may be used to render one or more data points or other information on a low power display (e.g., 142) or to energize one or more LEDs (e.g., 140).

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. A method for harvesting and using electrical energy during operation of a syringe, comprising:
    operating the syringe, wherein operating includes displacing a plunger of the syringe to draw fluid into a reservoir of the syringe or expel fluid from the reservoir of the syringe;
    converting, by an electrical generator that is integral with the syringe, motion associated with displacing the plunger into electrical energy and wherein the operating includes displacing the plunger of the syringe to draw fluid into the reservoir, and the method further comprises measuring a fill level of the reservoir; and
    using at least some of the electrical energy to at least temporarily store, in a memory component integral with the syringe, one or more data points associated with operation of the syringe.

2. The method of claim 1, wherein the one or more data points include the fill level.

3. The method of claim 1, wherein measuring the fill level of the reservoir includes detecting a capacitance of a capacitor contained within the reservoir.

4. The method of claim 1, wherein the operating includes displacing the plunger of the syringe to expel fluid from the reservoir, and the method further comprises utilizing at least some of the electrical energy to wirelessly transmit, from a low power wireless transceiver integral with the syringe to a remote computing device, one or more of the data points.

5. The method of claim 4, wherein the low power wireless transceiver is a Bluetooth low energy transceiver or a ZigBee transceiver.

6. The method of claim 1, further comprising utilizing at least some of the electrical energy to render, on a low power display integral with the syringe, one or more of the data points.

7. The method of claim 1, wherein the method further comprises utilizing at least some of the electrical energy to wirelessly receive, at a low power wireless transceiver integral with the syringe from a remote computing device, a timestamp.

8. An energy harvesting syringe, comprising:
    a housing;
    a plunger that is displaceable relative to the housing to draw fluid into a reservoir or to expel fluid from the reservoir;
    an electrical generator integral with the syringe, wherein the electrical generator converts motion associated with displacement of the plunger into electrical energy and wherein the displacement includes displacement of the plunger to draw fluid into the reservoir, and the one or more data points include a fill level of the reservoir that is detected using at least some of the electrical energy; and
    a memory component integral with the syringe, wherein the memory component is powered by at least some of the electrical energy to store one or more data points associated with operation of the syringe.

9. The energy-harvesting syringe of claim 8, further comprising two or more capacitive electrodes within the reservoir, wherein the fill level of the reservoir is measured by detecting a capacitance of the two or more capacitive electrodes.

10. The energy-harvesting syringe of claim 8, further comprising a low power wireless transceiver integral with the syringe, wherein the displacement includes displacement of the plunger to expel fluid from the reservoir, and at least some of the electrical energy is used to wirelessly transmit, from the low power wireless transceiver to a remote computing device, one or more of the data points.

11. The energy-harvesting syringe of claim 10, wherein the low power wireless transceiver is a Bluetooth low energy transceiver, a ZigBee transceiver, or an EnOcean transceiver.

12. The energy-harvesting syringe of claim 8, further comprising a low power display integral with the syringe, wherein at least some of the electrical energy is utilized to render, on the display, one or more of the data points.

13. The energy-harvesting syringe of claim 8, further comprising a low power wireless transceiver integral with the syringe, wherein at least some of the electrical energy is utilized to wirelessly receive, at the low power wireless transceiver from a remote computing device, a timestamp.

* * * * *